(12) United States Patent
Mikulak et al.

(10) Patent No.: US 10,090,669 B2
(45) Date of Patent: Oct. 2, 2018

(54) ENHANCED LIQUID DETECTION MECHANISMS FOR CIRCUIT CARDS

(71) Applicant: Systems and Software Enterprises, LLC, Brea, CA (US)

(72) Inventors: Steven Mikulak, Clark, NJ (US); Samuel Allen Carswell, Yorba Linda, CA (US); Joseph Rhoads Winston, Yorba Linda, CA (US)

(73) Assignee: SYSTEMS AND SOFTWARE ENTERPRISES, LLC, Brea, CA (US)

( * ) Notice: Subject to any disclaimer, the term of this patent is extended or adjusted under 35 U.S.C. 154(b) by 29 days.

(21) Appl. No.: 15/268,395

(22) Filed: Sep. 16, 2016

(65) Prior Publication Data
US 2017/0077694 A1    Mar. 16, 2017

Related U.S. Application Data

(60) Provisional application No. 62/219,561, filed on Sep. 16, 2015.

(51) Int. Cl.
| | |
|---|---|
| *G01R 27/26* | (2006.01) |
| *H02H 5/08* | (2006.01) |
| *G01N 27/04* | (2006.01) |
| *H05K 3/28* | (2006.01) |
| *H05K 1/02* | (2006.01) |
| *G01N 27/22* | (2006.01) |

(52) U.S. Cl.
CPC ........... *H02H 5/083* (2013.01); *G01N 27/048* (2013.01); *H05K 3/284* (2013.01); *G01N 27/223* (2013.01); *H05K 1/0213* (2013.01); *H05K 1/0268* (2013.01); *H05K 1/0272* (2013.01); *H05K 2201/09909* (2013.01); *H05K 2201/10151* (2013.01)

(58) Field of Classification Search
USPC ......................................................... 324/700
See application file for complete search history.

(56) References Cited

U.S. PATENT DOCUMENTS

| 4,297,686 A | 10/1981 | Tom | |
|---|---|---|---|
| 6,175,310 B1 * | 1/2001 | Gott ..................... | G01M 3/165 340/604 |
| 2005/0045493 A1 | 3/2005 | Mahurin et al. | |

(Continued)

FOREIGN PATENT DOCUMENTS

| EP | 2755023 A1 | 7/2014 |
|---|---|---|
| JP | 2000-162081 A | 6/2000 |
| WO | 2014/060894 A2 | 4/2014 |

*Primary Examiner* — Vincent Q Nguyen
(74) *Attorney, Agent, or Firm* — Umberg Zipser LLP; Ryan S. Dean

(57) ABSTRACT

Enhanced short circuit damage protection by using circuit card and electronic assembly features to steer liquids, including water, onto detector arrays. In a typical implementation, a circuit card has detection elements in one or more places implemented as artwork on an outer circuit layer. The finished circuit card assembly is conformal coated with masked areas over detection artwork. When the masking is removed, channels are left behind for liquids to flow toward and pool over detection artwork. In other implementations through shaping, additive or subtractive manufacturing processes, cavities are left behind for liquids to collect over detection artwork.

15 Claims, 4 Drawing Sheets

(56) References Cited

U.S. PATENT DOCUMENTS

2006/0125053 A1* 6/2006 Song .................... H01L 29/866
                                                    257/603
2013/0161086 A1* 6/2013 Mayer ................. H05K 5/0217
                                                    174/535
2014/0286825 A1   9/2014 Chen

* cited by examiner

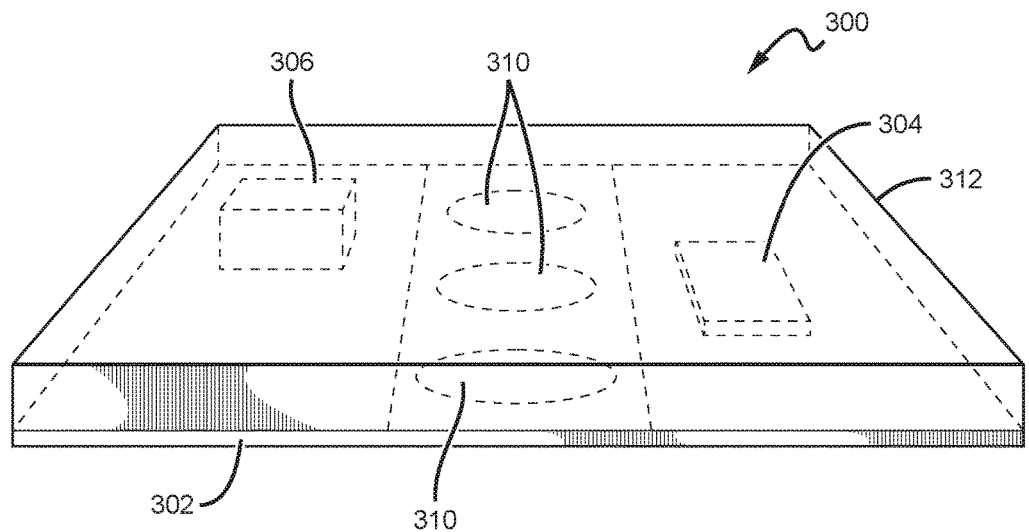
FIG. 4B
FIG. 4C
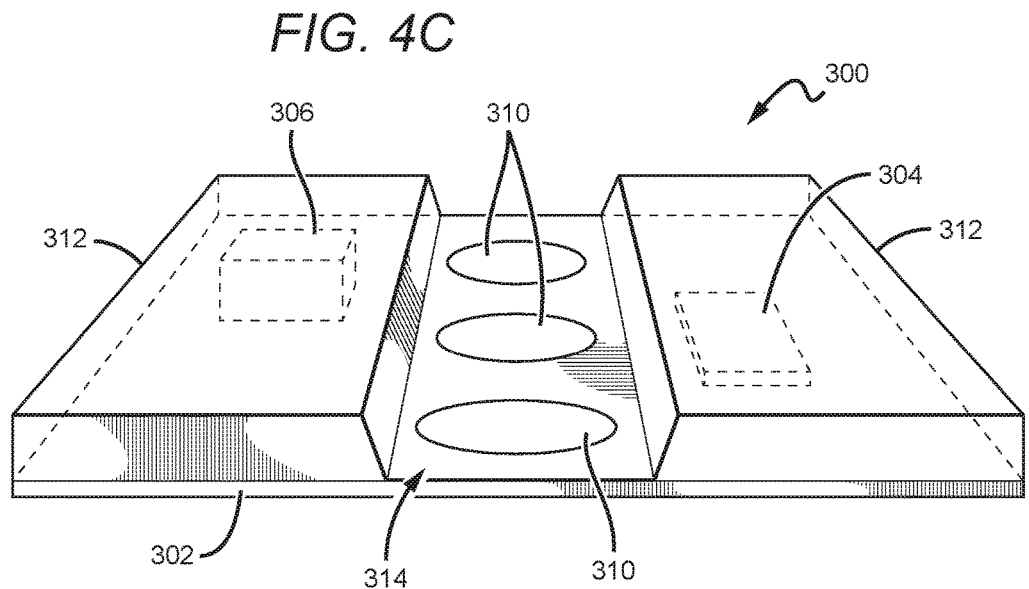

ENHANCED LIQUID DETECTION MECHANISMS FOR CIRCUIT CARDS

This application claims priority to U.S. provisional application having Ser. No. 62/219,561 filed on Sep. 16, 2015. All extrinsic materials identified herein are incorporated by reference in their entirety.

FIELD OF THE INVENTION

The field of the invention is circuit cards.

BACKGROUND

The background description includes information that may be useful in understanding the present invention. It is not an admission that any of the information provided herein is prior art or relevant to the presently claimed invention, or that any publication specifically or implicitly referenced is prior art.

Electronics present a safety hazard in environments where unintentional exposure to conductive liquids by dripping, spilling, submersion and condensation are possible. Ground fault detection provides protection from electric shock. Other failure mechanisms can produce smoke, arcing and other unintentional behavior that might otherwise go undetected. Sealed enclosures are in an option in some cases where cost and thermal performance are not critical factors. Cooling holes improve heat transfer but make waterproofing requirements difficult to meet.

Printed circuit boards (PCBs) are easily damaged by conductive liquids. Some have attempted to solve this problem by indiscriminately applying a hydrophobic coating to the PCB, but imperfections in the coating can lead to short circuit related hazards and damage, especially if the liquid is present for a long time as it eventually finds its way to exposed conductors.

Detection mechanisms for liquids have also been used. Liquids are often detected by resistive measurement between two electrodes. In its simplest form, such a detection element has two conductors side by side. When a conductive liquid is poured on top of the conductors, current can now flow between them. Detection circuitry picks up a change in voltage or current and some action is taken. For example, U.S. Pat. No. 4,297,686 discusses this technique, shutting off water in the event of pipe leaks to prevent flooding. This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

A very simple example of detection circuitry 100 is depicted in FIG. 1A, which illustrates a circuit with two conductive plates that serves as detection artwork. The term "artwork" is used here because the plates could be easily implemented as circles of exposed copper on an outer layer of a circuit card. A comparator in this example handles the detection. When a conductive liquid shorts the plates as shown in FIG. 1B, the comparator signals an alert by illuminating a light-emitting diode (LED).

Capacitive means have also been used to detect liquids. In a most basic form, such a mechanism utilizes two conductors spaced by a dielectric such as air or the substrate to which they are mounted. The conductors need not be exposed but will have a capacitance between them. As liquid approaches or contacts the sensing conductors, the dielectric properties between, and therefore capacitance between, the conductors is altered. This can then be detected by measuring circuitry and signal an action to be taken.

While these technologies each pose a potential solution to the problem of sensing liquids, they fail to address the need for the detectors to be exposed to the liquid before damage to other components may occur. In this manner, by the time the liquid is detected, damage may already have occurred.

Thus, there is still a need in the art for improved conductive liquid protection for PCBs.

SUMMARY OF THE INVENTION

The present invention provides apparatus, systems, and methods concerning channeling conductive liquids to liquid detection artwork on a PCB. In preferred embodiments, the presence of a conductive liquid can be detected before the PCB is damaged by the conductive liquid. Components of the PCB can be shut down upon detection of the conductive liquid, thus sparing the components from damage.

In one embodiment, a circuit card is coated such that components on the card are largely protected from liquids, while detection artwork remains exposed to allow sensors to quickly identify the presence of conductive liquid and send a signal that results in circuitry being powered down until it is again safe to operate (e.g., the conductive liquid is removed).

In other contemplated embodiments, a coating may not be necessary. Instead, the structure of the enclosure or components or features attached to the circuit card can be used to steer liquid towards detection artwork. Again, the detection artwork can then signal the presence of liquid to cause circuitry to be shut down.

It is also contemplated that circuit cards could include liquid steering in their structure at the time of manufacture. For example, etched or routed openings on the circuit cards can be used to channel liquid to detection artwork in lower layers. In one contemplated embodiments, copper shapes on the surface are physically raised relative to areas void of copper. This property of circuit card design may be exploited to steer and pool liquids around detection artwork.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIGS. 4A-4C shows an improved circuit card design concept such that the exposed detection artwork is the most susceptible component to the presence of liquids.

DETAILED DESCRIPTION

Figure 1A:
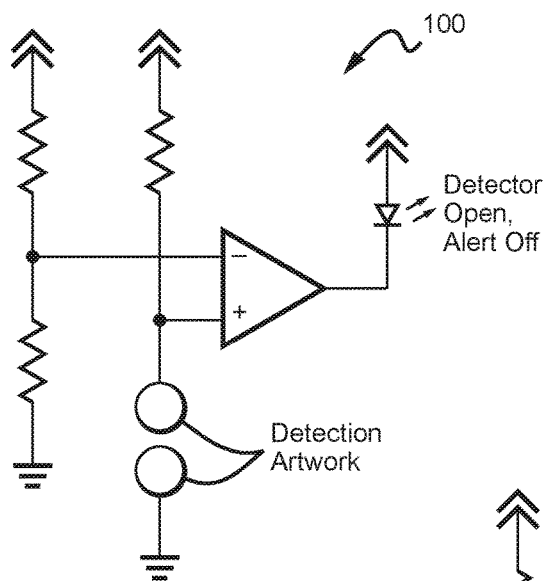
FIGS. 1A-1B shows a prior art circuit diagram to illustrate one possible implementation of simple detection artwork.
Figure 1B:
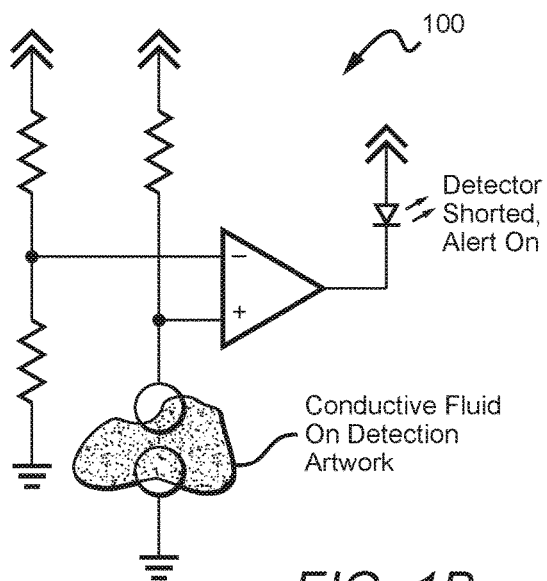

The following discussion provides example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Also, as used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment.

It should be noted that any language directed to a computer should be read to include any suitable combination of computing devices, including servers, interfaces, systems, databases, agents, peers, Engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network. The following description includes information that may be useful in understanding the present invention. It is not an admission that any of the information provided herein is prior art or relevant to the presently claimed invention, or that any publication specifically or implicitly referenced is prior art.

To prevent conductive liquids (e.g., water) from damaging a PCB, the inventors discovered that a printed circuit board can be configured via structure or components (i.e., using the PCB itself or materials added to the PCB) to route liquids toward detection artwork. The detection artwork can include one or more sensors with simple circuitry to power down electronics in the presence of conducting liquids. Such detection artwork can include, for example, shaped pads, vias, and traces. In this manner, when conductive fluid comes into contact with the detection artwork, such as that shown in the figures, a circuit is completed that can be used to directly or indirectly power down hazardous circuitry safely or signal that components should be powered down.

It is further contemplated that the PCB can include detection artwork that interferes with ingress of liquid into an electronics enclosure. For example, in some embodiments, the PCB can be printed to have features on its surface that direct the flow of liquid that comes into contact with the PCB to the detection artwork. Such features can include, for example, selectively raised coatings and etched, routed, or other topographic features that help to channel liquid. In still other embodiments, a coating can be selectively applied to the PCB such that liquid is steered across the PCB. In each of these embodiments, the result is that the conductive fluid is directed to the detection artwork and preferably away or at least not toward sensitive components.

Figure 2:
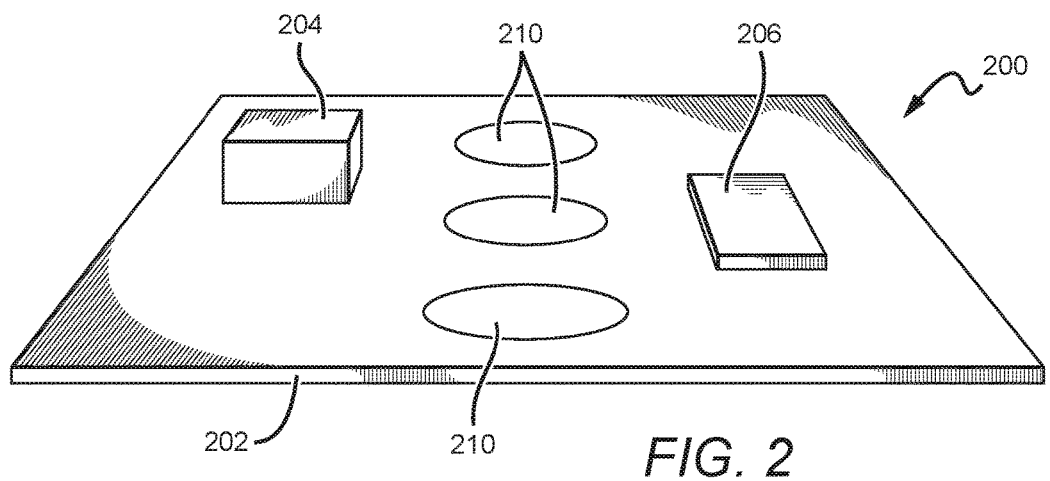
FIG. 2 is a perspective view of one embodiment of a circuit card assembly with liquid detection artwork etched into the circuit card beside other circuit components.

FIG. 2 depicts a typical circuit card assembly 200 comprising a circuit card 202 with various components 204, 206 disposed on the card 202. Liquid detection artwork 210 is etched into the circuit card 202.

Figure 3:
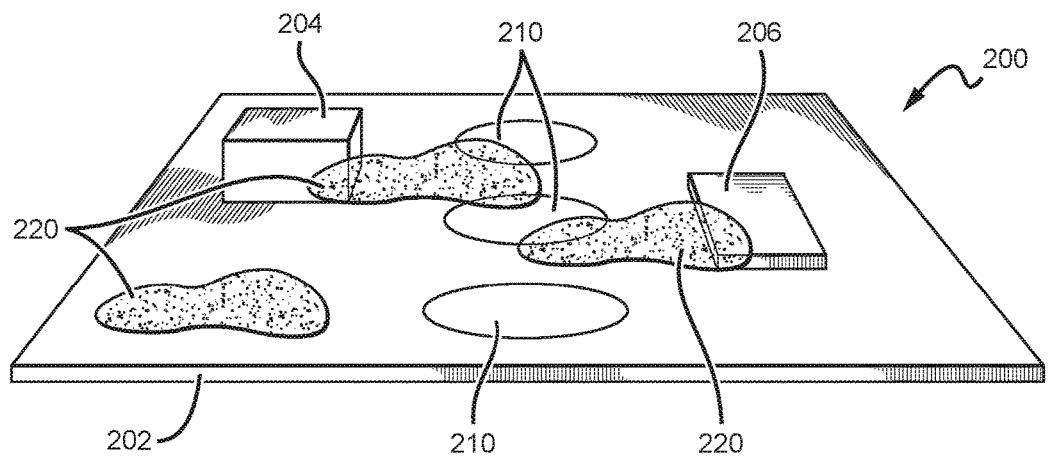
FIG. 3 shows the circuit card assembly of FIG. 2 with liquid present.

FIG. 3 illustrates circuit card assembly 200 of FIG. 2 having liquid 220 disposed on the card 202. Because of the card's configuration, components have as much as a probability of coming into contact with the liquid as the detection artwork 210.

Figure 4A:
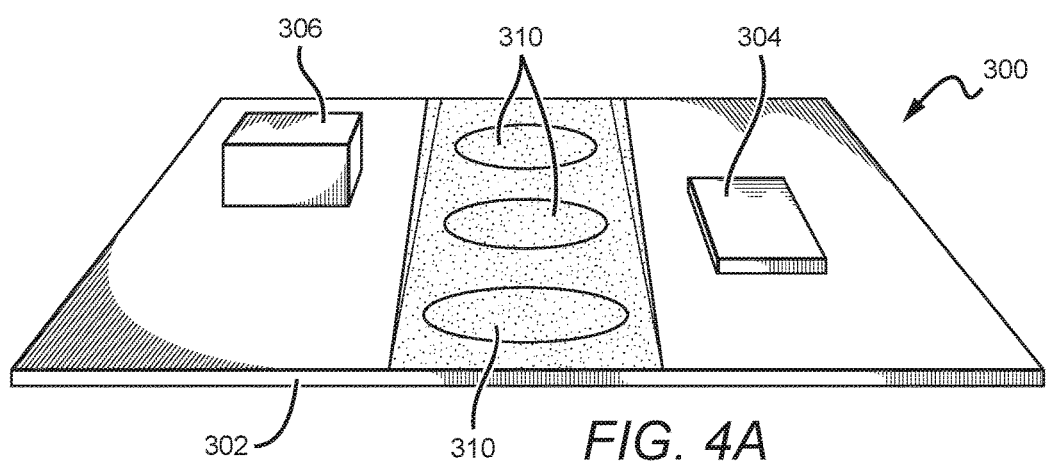

FIGS. 4A-4C depict the stages of manufacture of another embodiment of a circuit card assembly 300 comprising a circuit card 302. In FIG. 4A, the detection artwork 310 is first masked onto the card 302. In FIG. 4B, the circuit card 302 including the detection artwork 310 and components 304, 306 are coated with a coating 312. Finally, in FIG. 4C, the mask over the detection artwork 310 is stripped away leaving a channel 314, and exposing the detection artwork 310 while the other components 304, 306 remain coated. In such embodiment, the coated components 304, 306 are advantageously kept from being contacted with a liquid and the channel 314 can be used to direct liquid to the detection artwork 310.

Figure 5:
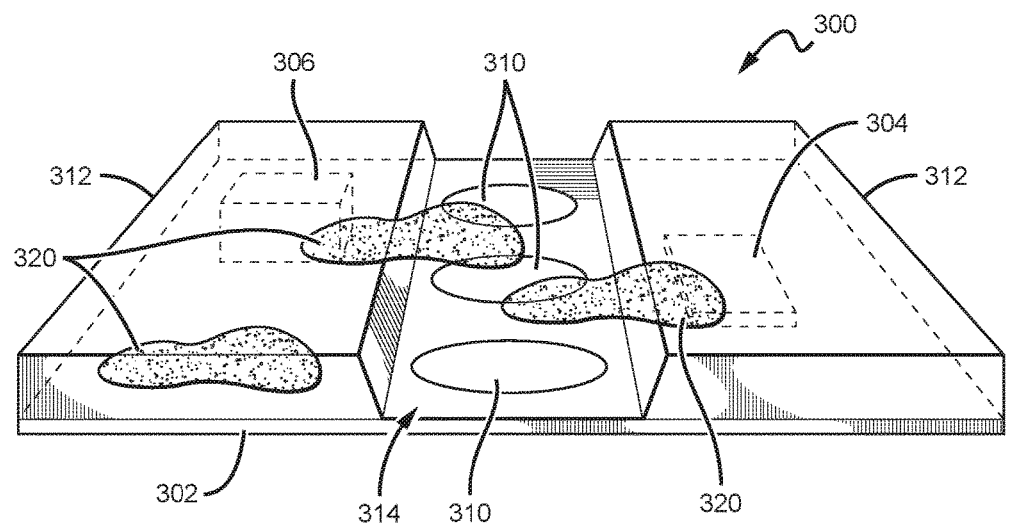
FIG. 5 shows the circuit card assembly of FIG. 4C with liquid present.

FIG. 5 shows the circuit card assembly 300 depicted in FIG. 4C exposed to liquid. In contrast to what is shown in FIG. 3, the coating 312 lowers the probability of component shorting. At the same time, the exposed detection artwork 310 has an increased probability of coming into contact with the liquid, as gravity will draw any standing liquid drops into the detection artwork 310, such as via channel 314.

In some embodiments, it is contemplated that the coating could be further tapered to provide a downward slope toward the channel 314 to further assist in directing liquid flow to the channel 314 and detection artwork 310.

Figure 6:
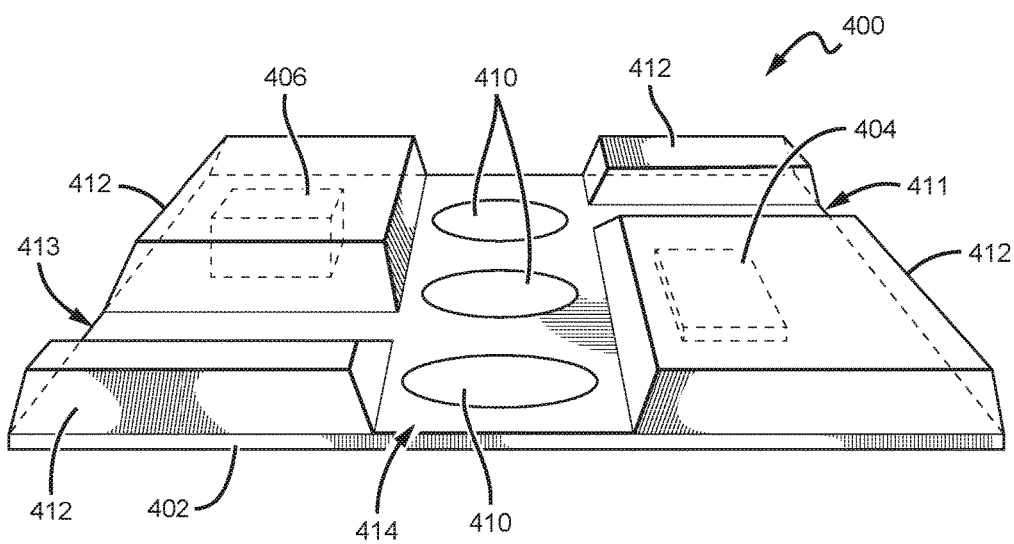
FIG. 6 shows another embodiment of a circuit card assembly structured to channel liquid flow along the circuit card.

All the figures thus far have dealt with liquid coming from the top. FIG. 6 depicts another embodiment of a circuit card assembly 400 having a circuit card 402 that includes channels 411, 413, which advantageously direct liquid flow laterally along the circuit card 402, such as to channel 414 and detection artwork 410. Again, gravity contains liquid within the channels 411, 413. By adding one or more additional channels, which preferably are approximately perpendicular to channel 414 that comprises detection artwork 410, the area of coverage of the detection artwork 410 is increased due to the increase number of paths or channels leading to the detection artwork 410.

These channels may or may not include features to slope toward the detection artwork.

Although the above examples discuss the deposition of a coating on a circuit card, other techniques could be used without departing from the scope of the inventive concepts described herein. For example, similar results can be accomplished by including on the circuit card routing channels, raised etches on the circuit card and its layers, or molded features placed over the top of circuits. Still further, inner layers of a circuit card could be used, drilling or cutting could be used, as well as other methods that expose underlying detection artwork.

Figure 7:
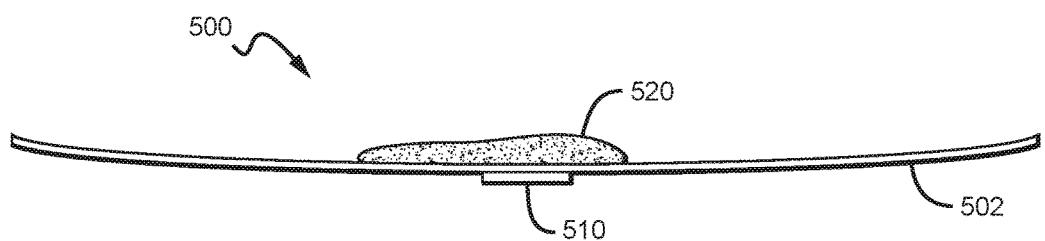
FIG. 7 shows another embodiment of a circuit card assembly having a curved or flex configuration.

FIG. 7 depicts a circuit card assembly 500 having a circuit card 502 with a curved or flex circuit configuration. In such embodiment, the card 502 can include exposed detection artwork 510 that signals when liquid is present. The flex or curved configuration of the circuit card 502 advantageously directs liquid to the detection artwork 510 (and away from components) via gravity. It is contemplated that a cable or flex assembly with selectively exposed conductors could be used as such the detection artwork 510. As used herein, the term "flex assembly" includes both flex cable and rigid flex. Contemplated flex assembly include, for example, simple wire in insulator type cables, flex cables and rigid flex assemblies that mix PCB and flex cable technologies.

Thus, specific compositions and methods of improving detection artwork for a circuit card have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure all terms should be interpreted in the broadest possible manner consistent with the context. In particular the terms "comprises" and "comprising" should be interpreted as referring to the elements, components, or steps in a non-exclusive manner, indicating that the referenced elements, components, or steps can be present, or utilized, or combined with other elements, components, or steps that are not expressly referenced.

What is claimed is:

1. A circuit card assembly, comprising:
   a circuit card having one or more components and a first and second channel;
   detection artwork disposed within the first channel;
   wherein the circuit card further comprises a coating on an upper surface of the circuit card; and
   wherein the first channel is defined on first and second sidewalls by the coating, and the first channel is configured to direct liquid present on the circuit card to the detection artwork, wherein the second channel is arranged in a direction that is perpendicular to a direction of the first channel, and wherein the second channel is defined on first and second sidewalls by the coating.

2. The circuit card assembly of claim 1, further comprising one or more components disposed on the circuit card and underneath the coating.

3. The circuit card assembly of claim 1, wherein the detection artwork comprises shaped pads, vias, or traces.

4. The circuit card assembly of claim 1, wherein the detection artwork comprises a sensor configured to send a signal when a liquid is present.

5. A circuit card assembly, comprising:
   a circuit card having one or more components and a first and second channel;
   detection artwork disposed within the first channel;
   wherein the circuit card further comprises a coating on an upper surface of the circuit card; and
   wherein the first channel is defined on first and second sidewalls by the coating, and the first channel is configured to direct liquid present on the circuit card to the detection artwork, wherein the second channel is arranged in a direction that is perpendicular to a direction of the first channel, and wherein the first and second channels intersect.

6. A circuit card assembly, comprising:
   a circuit card having one or more components and a first and second channel;
   detection artwork disposed within the first channel;
   wherein the first channel is defined on first and second sidewalls by at least one of raised etches, routing channels, and molded features; and
   wherein the first channel is configured to direct liquid present on the circuit card to the detection artwork, wherein the second channel is arranged in a direction that is perpendicular to a direction of the first channel, and wherein the first and second channels intersect.

7. The circuit card assembly of claim 6, wherein the first channel is defined by raised etches.

8. The circuit card assembly of claim 6, wherein the first channel is defined by routing channels.

9. The circuit card assembly of claim 6, wherein the first channel is defined on first and second sidewalls by molded features.

10. The circuit card assembly of claim 6, wherein the detection artwork comprises shaped pads, vias, or traces.

11. The circuit card assembly of claim 6, wherein the detection artwork comprises a sensor configured to send a signal when a liquid is present.

12. A method of forming a circuit card assembly having one or more components and an exposed detection artwork, comprising:
    applying a mask to a detection artwork disposed on a circuit card;
    after the mask is applied, coating the circuit card and detection artwork;
    removing the mask over the detection artwork to form a channel and expose the direction artwork; and
    wherein first and second sidewalls of the channel are defined by the coating, and wherein the detection artwork comprises a sensor configured to send a signal when a liquid is present.

13. The method of claim 12, removing the coating from a second portion of the circuit card to form a second channel.

14. The method of claim 13, wherein the second channel is defined on first and second sidewalls by the coating, and wherein the second channel intersects with the channel.

15. The method of claim 12, wherein the detection artwork comprises shaped pads, vias, or traces.

* * * * *